United States Patent [19]  
Gerard

[11] Patent Number: 5,066,441  
[45] Date of Patent: Nov. 19, 1991

[54] PROCESS FOR COMPACTING A CALCIUM PHOSPHATE COMPOSITION

[75] Inventor: Thomas W. Gerard, Upper Saddle River, N.J.

[73] Assignee: Rhone-Poulenc Basic Chemicals Co., Shelton, Conn.

[21] Appl. No.: 206,937

[22] Filed: Jun. 6, 1988

Related U.S. Application Data

[63] Continuation of Ser. No. 746,468, Jun. 20, 1985, abandoned, which is a continuation-in-part of Ser. No. 682,570, Dec. 14, 1984, abandoned, which is a continuation of Ser. No. 594,424, Mar. 29, 1984, abandoned, which is a continuation of Ser. No. 444,009, Nov. 23, 1982, abandoned, which is a continuation of Ser. No. 215,953, Dec. 12, 1980, abandoned.

[51] Int. Cl.$^5$ .............................................. B29B 9/12
[52] U.S. Cl. ................................. 264/118; 23/293 R; 264/109; 264/175; 423/311; 424/602
[58] Field of Search .............. 23/293 R; 264/37, 109, 264/118, 117, 280, 349, 175; 106/193 R; 422/243; 423/311; 425/111, 112; 424/128, 602; 426/517, 518, 563; 536/56; 241/3

[56] References Cited

U.S. PATENT DOCUMENTS

| | | | |
|---|---|---|---|
| 1,534,828 | 4/1925 | Barr | 264/109 X |
| 1,935,575 | 11/1933 | Neuberg | 23/293 R X |
| 2,160,232 | 5/1939 | Schlaeger | 426/563 |
| 2,436,771 | 2/1948 | Hood | 23/293 R X |
| 2,663,907 | 12/1953 | Downing et al. | 264/349 X |
| 2,847,710 | 8/1958 | Pitzer | 264/109 |
| 3,042,668 | 7/1962 | Monti et al. | 424/361 X |
| 3,134,719 | 5/1964 | Sheth et al. | 424/229 X |
| 3,146,168 | 8/1964 | Battista et al. | 424/360 X |
| 3,181,998 | 5/1965 | Kanig | 424/94 X |
| 3,344,030 | 9/1967 | Stevens et al. | 424/362 X |
| 3,357,845 | 12/1967 | Battista | 106/193 R |
| 3,396,226 | 8/1968 | Cavalli et al. | 424/362 X |
| 3,433,863 | 3/1969 | Bowden et al. | 23/293 R X |
| 3,441,387 | 4/1969 | Dye | 23/293 R X |
| 3,564,083 | 2/1971 | Fournet et al. | 264/37 |
| 3,564,097 | 2/1971 | Magid | 424/128 X |
| 3,639,168 | 2/1972 | Monti et al. | 424/361 X |
| 3,639,169 | 2/1972 | Broeg et al. | 424/361 X |
| 3,821,414 | 6/1974 | Monti | 424/361 |
| 3,883,647 | 5/1975 | Geller | 424/362 X |
| 3,904,726 | 9/1975 | Jacquelin et al. | 264/37 X |
| 4,159,346 | 6/1979 | Omura et al. | 424/362 |
| 4,248,601 | 2/1981 | McGough et al. | 23/293 R |
| 4,283,423 | 8/1981 | Watkins et al. | 426/517 X |

FOREIGN PATENT DOCUMENTS 1245830 9/1971 United Kingdom ............... 426/517

OTHER PUBLICATIONS

Gandel, V. G.: *Chemical Abstracts*, 70, p. 220, 109146y (1969).

*Primary Examiner*—Richard L. Chiesa
*Attorney, Agent, or Firm*—Paul J. Juettner

[57] ABSTRACT

A process for treating calcium phosphate fine particles which includes the step of compacting the particles under pressure to form a sheet.

10 Claims, No Drawings

PROCESS FOR COMPACTING A CALCIUM PHOSPHATE COMPOSITION

This application is a continuation of application Ser. No. 746,468 filed on June 20, 1985, now abandoned, which is a continuation-in-part of application Ser. No. 682,570 filed on Dec. 14, 1984, now abandoned, which is a continuation of application Ser. No. 594,424, filed on Mar. 29, 1984, now abandoned, which is a continuation of application Ser. No. 444,009 filed on Nov. 23, 1982, now abandoned, and which is a continuation of application Ser. No. 215,953 filed on Dec. 12, 1980, also now abandoned.

BACKGROUND OF THE INVENTION

This invention relates to compacting fine particles of calcium phosphate. More particularly the invention relates to compacting fine particles of calcium phosphate material, e.g. dicalcium phosphate dihydrate, tricalcium phosphate, monocalcium phosphate, and calcium pyrophosphate to form ribbons or sheets as a preparatory step to utilizing the compacted material for later processing, for example, as excipients in pharmaceutical tablets.

Granules of calcium phosphate sized from about 75 micrometers (um) to about 450 um have great utility as excipients in the manufacture of pharmaceutical tablets, as food supplements for humans or animals, and in the beverage and baking industries. Fine particles, that is particles from about 1 um to about 75 um in size, however, present great problems in handling. Fine particles dust readily, do not flow easily, are burdensome to transport and store, and have too low a bulk density to be utilized directly in tabletting and other processing equipment.

U.S. Pat. No. 2,847,710 granted in 1958 to Pitzer discloses a process for improving the fluid properties of powdered solid materials such as phosphate rock by forming an intimate dry mixture of the powder with about 10 percent of its weight of a solid combustible organic binder-lubricant with a melting point below that of the powdered solid, heating the mixture to melt the organic binder-lubricant, cooling the mixture to a temperature below the melting point of the binder-lubricant, and pelleting the mixture by causing it to flow into small dies, and compressing the pellets.

Gandel discloses in the Chemical Pharmaceutical Journal of the USSR 1969, 3(2), pp 51–56, as abstracted in Chemical Abstracts 70, page 220, 109146 y (1969), a process for granulation of moistened calcium acid phosphate by pressing it through a perforated plate with 0.5 mm holes and then tabletting the compacted material.

U.S. Pat. No. 1,534,828 granted in 1925 discloses the use of phosphoric acid as a binder in briquetting phosphate rock in a "Belgian roll" machine at about 550 atmospheres pressure.

U.S. Pat. No. 3,564,097 granted to Magid in 1971 discloses the use of tricalcium phosphate particles smaller than 75 um as excipients in tablets after they have been mixed with other ingredients and granulated with water. After drying, the large granules are milled, mixed with other ingredients, and the powder compressed into tablets.

U.S. Pat. No. 3,821,414 granted to Monti in 1974 discloses the use of an aqueous solution of locust bean gum as a binder for fine tricalcium phosphate particles 45 um to 75 um in diameter so that the phosphate can be employed as an excipient in making compressed tablets or wafers.

It is an object of the invention to provide a process for utilizing fine particles of calcium phosphate less than 75 um in size. A further object of the invention is to provide compacted sheets or ribbons of calcium phosphate. Still another object of the invention is to make granules of compacted calcium phosphate from about 75 to about 450 um in diameter. An additional object of the invention is to utilize fine particles of dicalcium phosphate dihydrate, tricalcium phosphate, and calcium pyrophosphate as excipients in the production of pharmaceutical tablets or wafers.

SUMMARY OF THE INVENTION

Surprisingly, we have found that fine particles, ranging in size from about 1 um to about 75 um, of calcium phosphate material, e.g. dicalcium phosphate dihydrate, tricalcium phosphate, monocalcium phosphate, or calcium pyrophosphate can be compacted under sufficient mechanical load into pellets, sheets or ribbons at ambient temperature. The process of the invention can be carried out statically in a hydraulic press to make a sheet or dynamically between a pair of counterrotating rolls to make a ribbon of compacted calcium phosphate.

The pellets, sheets, or ribbons of compacted calcium phosphate consist essentially of compacted powder from about 80 to about 400 um in diameter. The compacted calcium phosphate may be comminuted into chips, flakes, or granules of various sizes from about 5 mm to about 50 mm. The chips, flakes, or granules may be in turn ground to produce powder useful as an excipient in producing pharmaceutical tablets.

DETAILED DESCRIPTION OF THE INVENTION

Phosphoric acid is neutralized by compounds containing calcium, such as lime, to form various solid forms of calcium phosphate. Among these calcium phosphates are monocalcium phosphate, $Ca(H_2PO_4)_2$, either anhydrous or monohydrated; dicalcium phosphate, $CaHPO_4$, either anhydrous or dihydrated; tricalcium phosphate, hydroxyapatite, $Ca_5(PO_4)_3(OH)$, and calcium pyrophosphate, $Ca_2P_2O_7$. In the course of producing commercial quantities of calcium phosphates, fine particles are generated. Fine particles of calcium phosphate less than about 75 um in diameter flow poorly, cause handling problems due to dusting, storage problems due to large volume, and have too low a bulk density to be readily moldable.

The present invention is a process for compacting by mechanical pressure fine calcium phosphate particles from about 1–75 um in size to form larger particles about 80–400 um in size. The compacted material flows easily, dusts much less, and can be directly tabletted as an excipient into pharmaceutical tablets with conventional tabletting equipment.

The conversion from fine particles of calcium phosphate with properties unsuitable for many commercial applications to useful granules of calcium phosphate, hitherto unknown, is carried out in two steps: a compaction step and a comminution step.

The compaction step can be carried out at a slow rate by the application of mechanical force, such as that found in a hydraulic press to produce a sheet. For example, if 7350 lbs. (3334 kg.) of applied load is applied to the sample in a laboratory hydraulic press measuring about 15 to 20 centimeters (cm) on each side, the rate of application of applied load is about 735–1470 lbs. (333.4–666.8 kg) second.

The compaction step can also be carried out at a high rate of application of pressure. If the calcium phosphate fine powder is fed into the nip between two rolls counterrotating from about 3 to about 100 rpm and generating up to about 18,000 lbs of force per linear inch of roll width in an industrial rolling press to produce a ribbon of compacted material. Irrespective of the rate of application of force, which is determined by the type of apparatus employed, the actual pressure employed for the compaction step can vary from about 4,000 lbs. force per linear inch of roll width to about 18,000 lbs. force per linear inch of roll width or higher. The preferred range in applied pressure for compaction is from about 8,000 lbs. force per linear inch of roll width to about 14,000 lbs. force per linear inch of roll width.

The size of the sheet or ribbon produced by compaction is determined by the apparatus employed. A laboratory compression mold plunger makes a circular tablet approximately 1.25 cm in diameter. A laboratory press makes a sheet about 10 cm to 40 cm square. Commercial rolling presses are available to produce a ribbon from about 6 cm to about 60 cm wide. The thickness in the case of the compression mold plunger and the hydraulic press is determined by the amount of fine powder charged. In the case of the rolling press, the thickness of the ribbon produced is determined by the rate of feed of fine particulate powder into the nip between the rolls, as well as the configuration of the rolls and the pressure applied to the rolls.

The particle size of the fine powder used as the feed material varies from about 1 um to about 75 um. Submicron size calcium phosphate has utility as a suspension aid, dietary supplement, or additive in insecticides. Crystals of calcium phosphate larger than about 500 um are employed directly to produce super phosphate or triple super phosphate. The products of the present invention, powder from about 75 um to about 425 um in size, are suitable for tabletting. For tricalcium phosphate, and calcium pyrophosphate this size granule has been hitherto unavailable to industry.

The bulk density of the fine particle feed to the compacting process of the present invention ranges from about 0.15 to about 0.5 g/cc (10–30 lbs/ft$^3$). A bulk density of about 0.3 g/cc (20 lbs/ft$^3$; minus 325 mesh) is preferred. The bulk density of the compacted and comminuted product of the instant invention varies from about 0.4 g/cc to about 1.2 g/cc (25–75 lbs/ft$^3$).

The surface of the rolls or plates applying the mechanical force can be scored to give corrugated, patterned, or briquetted compacted product of any desired shape. Corrugations facilitate the flow of the fine feed into the nip of the rolls.

When rolls are used to produce compacted calcium phosphate in ribbon form, they rotate at any speed from about 3 to about 100 rpm. Within this range a speed of from about 4 to about 20 rpm is preferred in the practice of the process of the instant invention.

The invention can be carried out at ambient humidity and ambient temperature. The compaction step in exerting mechanical pressure on the fine particles of calcium phosphate by means of rolls increases the temperature of the calcium phosphate from about 10° to about 30° C. There is no need to chill the pressure rolls unless the temperature increases to the point where discoloration of the compacted calcium phosphate commences. The process of the invention is performed with calcium phosphate at a pH within the range of 2 to 10. A pH of about 6.4 to about 8.5 is preferred.

Preferably the comminution step is carried out in two steps: prebreaking and grinding. The compacted ribbon or sheet of calcium phosphate can be broken up into flakes, chips, slices, or pieces by standard cutting machines. It is convenient to attach a rotating set of cutting knives just below the compacting chamber of a continuous rolling press so that the ribbon of compacted calcium phosphate is immediately broken up into pieces varying in size from about 5 mm to 50 mm. The speed of rotation of the prebreaking knives varies from about 40 to about 1000 rpm, thus determining the size of the pieces. In practicing the instant invention, a prebreaking step for the compacted calcium phosphate is not required.

To be useful as tabletting excipients, nutrients in human food or animal feed, or for industrial uses, compacted calcium phosphate is ground to a size of from about 80 um to about 400 um having a bulk density of from about 0.4 to about 1.2 g/cc. The preferred bulk density for excipients in tabletting equipment is about 0.6 g/cc to about 1.1 g/cc.

Grinding mills such as those manufactured by the Fitzpatrick Co., Elmhurst, Ill.; Pulverizing Machinery Co., Summit, N.J.; and Raymond Division of Combustion Engineering Co., Stamford, Conn., may be used to prepare the desired, sized calcium phosphate from compacted sheet, ribbon, flakes, or chips of that material. The particle size of the comminuted calcium phosphate is determined by a number of parameters in a grinding mill among which are the number of cutting blades, the shape of the cutting blades, the speed of rotation of the blades, the size of the screen employed, the shape of the holes in the screen, the type of feed throat, the pattern at which the blades are set, and the rate at which the feed is fed into the comminutor.

The usual comminutor is constructed within a cylindrical housing containing a rotor carrying sets of radial knives or hammers. The width of the preferred mill varies from about 15 to about 75 cm. The knives or hammers vary in a preferred mill from about 12 to about 80 in number with a radius of from about 12 to about 25 cm. The speed of rotation varies from about 800 to about 10,000 rpm. Rotating blades are either swinging or fixed to the rotor and are available in a variety of straight, curved, or stepped shapes. Preferred blades can have dull impact edges, which have a pulverizing function, or sharp cutting edges.

Comminuting blades may be assembled in various arrays. A preferred array has knife edges on one side and impact edges on the other. By changing the direction of rotation the degree of size reduction can be controlled. Blades can be mounted in aligned or precessing configuration. Screens may have round or square perforations, diagonal or straight slots, or may be a wire mesh—all of varying size from about 1 mm to about 5 mm. For a given screen and a given set of blades, the speed of rotation influences the amount of comminution. The higher the speed of the blade the more elliptical a round screen hole appears to a particle, hence the smaller the resulting size.

The design and location of the throat feeding the compacted material into a mill influences the particle size and distribution of particle size of the product. Because the granule approaches the screen directly, the more vertical the inlet for the feed, the fewer the fines produced, other parameters holding constant. The more horizontal the inlet for the feed, the finer the grind produced, since more metal surface is presented for cutting and rebounding. Among the preferred throats for feeding are wide pans, angular throats, vertical throats, horizontal throats, vertical cones, and sigmoidal throats.

The constancy of rate of feed into a comminutor and the rate, itself, determines the residence time, all other factors held constant. The degree of milling and the narrowness of the particle size distribution are also functions of residence time.

The present invention is illustrated by, but not limited by, the following examples. Other alternatives can be employed but still are encompassed within the scope of the present invention.

EXAMPLE 1

This Example illustrates that calcium phosphates were found by compression on a laboratory hydraulic press to be suitable for compaction on a roller press.

Tricalcium phosphate fine particles and dicalcium phosphate dihydrate fine particles alone, with 0.5 percent magnesium stearate, and alternatively with 5.0 percent locust bean gum, or guar gum, or gum arabic, or carboxymethyl cellulose were drymixed for five minutes on a rolling mill.

Then each mixture was poured into tabletting molds holding 0.75 g. per tablet and compressed into tablets on a laboratory hydraulic press under two conditions:
a) instantly at 24,000 lbs. (10,886 kg.) or
b) 30 seconds at 500 lbs. (227 kg.), followed by one minute at 8,000 lbs. (3629 kg.).

The tablets made at 24,000 lbs. (10,886 kg.) force all measured above 28 Strong Cobb Units (SCU) on a Schleuniger tablet hardness tester. The tricalcium phosphate and dicalcium phosphate dihydrate tablets containing only 0.5 percent magnesium stearate additive and compressed at 8,000 lbs. (3629 kg.) force broke at 6.3 SCU; those containing the gums also withstood 24 or more SCU.

EXAMPLE 2

This Example illustrates the use of a large laboratory roller press to compact dicalcium phosphate dihydrate.

Three compacting runs were carried out on dicalcium phosphate dihydrate using a compacting machine with counterrotating rolls 10 cm wide and 25 cm in diameter. The initial air classified fine powder had a moisture content of 7.8 percent by the Cenco moisture balance method, a loose bulk density of 0.74 g/cc, a tapped bulk density of 1.06 g/cc, and a size of −325 mesh. The runs were carried out at ambient temperature with the rolls counterrotating at 10 rpm.

For the first two runs the total hydraulic force was 3,510 kg/cm linear (19,650 lbs/in linear), the feed rate of fines was 381.5 kg/hr, the ribbon thickness 6.4 mm, and the yield of compacted material was 84 percent larger than 16 mesh (1.18 mm).

In the third run the same feed of fine particles was used at a rate of 36.1 kg/hr, the total hydraulic force was 2,504 kg/cm linear (14,020 lbs/in linear), and the yield of ribbon 6.4 mm thick gave 79 percent compacted material greater than 16 mesh (1.2 mm).

EXAMPLE 3

This Example illustrates the use of a comminuting mill to grind compacted calcium phosphate.

Without a prebreaker the compacted product of Example 2 was fed through a "vegetable" hooded pan throat into a 15-cm mill equipped with 16 sharp-edged knives mounted on a 27-cm diameter rotor revolving at 1500 rpm. The milled, compacted dicalcium phosphate produced had the following screen analysis.

| Screen | Percent by Weight | um |
| --- | --- | --- |
| +40 | 3.7 | 425 |
| +60 | 9.5 | 250 |
| +100 | 34.9 | 150 |
| +200 | 28.9 | 75 |
| −200 | 23.0 | 75 or smaller |

In the same comminution mill the product of Example 2 was ground at 2000 rpm with the following results.

| Screen | Percent by weight | um |
| --- | --- | --- |
| +40 | 0.8 | 425 |
| +60 | 3.8 | 250 |
| +100 | 29.0 | 150 |
| +200 | 36.6 | 75 |
| +325 | 13.6 | 45 |
| −325 | 16.2 | 45 or smaller |

EXAMPLE 4

This Example illustrates compaction of tricalcium phosphate on a rolling mill at moderate and high pressure.

Dried tricalcium phosphate fine powder having one percent moisture, a bulk density of 0.32 g/cc, and smaller than 45 um in size was fed into a rolling mill compactor fitted with 3.75 cm wide rolls, 20 cm in diameter revolving at 7 rpm at ambient temperature, which by friction heated the product to 55° C.

The applied linear force on the rolls was varied from 900 kg/cm to 1575 kg/cm to 3,510 kg/cm. In all cases the yield of compacted material larger than 425 um (+40 mesh) was 87.1 percent.

EXAMPLE 5

This Example illustrates the effect of varying the speed of rotation of a comminution mill while grinding compacted tricalcium phosphate.

The compacted tricalcium phosphate made in Example 4 was fed into the same comminution mill of Example 3 equipped with the same type of knives as in Example 3 equipped with a 40-mesh (0.43 mm) screen. As the speed of rotation increased the particle size distribution varied as follows:

| Sieve Size | RPM 1000 Wgt. Percent | RPM 1500 Wgt. Percent | RPM 1700 Wgt. Percent |
| --- | --- | --- | --- |
| +40 | trace | 5.9 | 2.5 |
| +60 | 11.6 | 25.5 | 25.5 |
| +100 | 13.8 | 16.9 | 21.0 |
| +120 | 4.2 | 4.8 | 5.7 |
| +200 | 27.8 | 11.7 | 9.5 |
| +325 | 41.5 | 34.6 | 33.3 |
| −325 | 1.0 | 0.6 | 2.1 |

EXAMPLE 6

This Example illustrates the effect of changing applied load while compacting dicalcium phosphate dihydrate with a rolling mill.

The sample of air-classified dicalcium phosphate smaller than 325 mesh (45 um) in particle size and having one percent moisture was fed into a 3.75-cm wide rolling mill with 20-cm diameter rolls counterrotating at seven rpm at ambient temperature. The degree of compaction measured by percent of product greater than 35 mesh (0.5 mm) varied with linear applied force as follows:

| Total force (kg/cm) | 1570 | 1750 | 2233 | 4200 | 4485 |
|---|---|---|---|---|---|
| Percent compaction | 80 | 80.9 | 81.5 | 73 | 86 |

EXAMPLE 7

This Example illustrates the comminution of compacted dicalcium phosphate under varying conditions.

On the same comminution mill as in Example 3, the compacted dicalcium phosphate of Example 6 was ground with the following results:

| Force of Compaction (kg/cm) | 1570 | 1570 | 1570 | 4200 |
|---|---|---|---|---|
| Comminution rpm | 1500 | 1500 | 1000 | 1000 |
| Mill screen size (mm) | 0.5 | 0.5 | 0.5 | 0.5 |
| Mill knives | impact | sharp | sharp | sharp |
| +40 sieve (.43 mm) wgt. % | trace | 0.1 | 0.2 | 0.2 |
| +60 sieve (.25 mm) wgt. % | 1.8 | 10.2 | 7.0 | 11.1 |
| +100 sieve (.15 mm) wgt. % | 9.5 | 15.4 | 12.4 | 14.1 |
| +140 sieve (.13 mm) wgt. % | 6.4 | 7.2 | 7.5 | 6.9 |
| +200 sieve (75 um) wgt. % | 26.6 | 16.3 | 17.5 | 18.6 |
| +325 sieve (45 um) wgt. % | 54 | 40.4 | 46.1 | 41.1 |
| −325 sieve wgt. % | 1.7 | 10.4 | 10.5 | 8.0 |
| Force of Compaction (kg/cm) | 4200 | 1750 | 2233 | 4485 |
| Comminution rpm | 1000 | 1500 | 1500 | 1500 |
| Mill screen size (mm) | 0.8 | 0.7 | 0.7 | 0.7 |
| Mill knives | sharp | sharp | sharp | sharp |
| +40 sieve (.43 mm.) wgt. % | trace | 3.1 | 4.3 | 3.5 |
| +60 sieve (.25 mm) wgt. % | trace | 13.5 | 16.1 | 15.6 |
| +100 sieve (.15 mm.) wgt. % | 5.9 | 10.9 | 12.2 | 11.3 |
| +140 sieve (.13 mm) wgt. % | 11.1 | 13.7 | 15.7 | 14.1 |
| +200 sieve (75 um) wgt. % | 38.0 | 8.9 | 6.7 | 7.4 |
| +325 sieve (45 um) wgt. % | 37.3 | 17.2 | 13.3 | 9.4 |
| −325 sieve wgt. % | 7.3 | 32.8 | 31.4 | 38.7 |

EXAMPLE 8

This Example illustrates the compaction of tricalcium phosphate on a rolling mill with various forces applied.

A dried sample of tricalcium phosphate fine powder, less than 40 um in size, with less than one percent moisture, and a bulk density of 0.32 g/cc was fed into the nip of a rolling press with 3.75 cm by 20 cm rolls counterrotating at seven rpm at a rate of 37.3 kg/hr at ambient temperature. The degree of compaction, measured by the weight percent greater than 0.5 mm in diameter, was as follows:

| Linear force applied (kg/cm) | 1610 | 2245 | 1350 |
|---|---|---|---|
| Compaction (%) | 96 | 90 | 89 |

These samples were then comminuted in the same mill as that of Example 7 at 1500 rpm bearing sharp knives and a 0.7 mm screen with the following results:

| | Compaction Force for Feed (kg/cm) | | |
|---|---|---|---|
| Screen Size | 1610 | 2245 | 1350 |
| +40 mesh | 4.8 | 6.0 | 4.8 |
| +60 mesh | 24.4 | 28.0 | 24.0 |
| +100 mesh | 18.0 | 18.0 | 17.6 |
| +140 mesh | 10.0 | 9.6 | 9.6 |
| +200 mesh | 7.6 | 6.8 | 7.6 |
| +325 mesh | 12.0 | 14.4 | 12.4 |
| −325 mesh | 23.2 | 17.2 | 24.0 |

EXAMPLE 9

This Example illustrates the compaction of a sample of dicalcium phosphate dihydrate containing five weight percent gum as a binder.

A sample of air-classified dicalcium phosphate dihydrate previously dry mixed with five percent by weight guar gum, having a bulk density of 0.8 g/cc was compacted on the same rolling mill as in Example 8 with the following results:

| Linear force applied (kg/cm) | 1610 | 4490 | 2232 |
|---|---|---|---|
| Compaction (wgt. % 0.5 mm) | 82.6 | 81.7 | 81.0 |

These compacted products were comminuted as in Example 8 with the following results:

| | Linear force applied (kg/cm) | | |
|---|---|---|---|
| Screen Size | 1750 | 5000 | 2250 |
| +40 mesh | 3.2 | 4.0 | 3.1 |
| +60 mesh | 12.0 | 14.4 | 11.2 |
| +100 mesh | 11.2 | 11.2 | 10.2 |
| +140 mesh | 9.2 | 9.6 | 11.2 |
| +200 mesh | 8.0 | 7.2 | 9.3 |
| +325 mesh | 11.6 | 10.4 | 15.1 |
| −325 mesh | 44.8 | 43.2 | 39.9 |

EXAMPLE 10

This Example illustrates the application of the present invention on a commercial scale over a four-day period.

Dried fine tricalcium phosphate with a particle size of about 40 um and a bulk density of 0.35 g/cc in the amount of 5,000 kg was fed into the hopper of a rolling mill compactor with grooved cylinder rolls 10 cm wide and 25 cm in diameter at the rate of about 180 kg/hr at ambient temperature. The total linear hydraulic force of the rolls was 580 kg/cm. Compaction efficiency, determined by the weight percent product greater than 0.5 mm in size was 97 percent.

The compacted material was immediately ground in a comminution mill 15 cm wide with a rotor 28 cm in diameter fitted with 16 sharp knives rotating at 2250 rpm. The comminution screen had 1.3 mm holes. Particles larger than 0.43 mm were recycled to the comminution mill. The final product had a bulk density of 0.72 g/cc. Sieve analysis of the compacted and comminuted tricalcium phosphate gave the following results:

| Sieve Size | Wgt. Percent |
|---|---|
| +40 | 2.3 |
| +60 | 27.0 |
| +100 | 18.4 |
| +140 | 7.8 |
| +200 | 7.5 |
| +325 | 25.4 |
| −325 | 10.9 |

EXAMPLE 11

This Example illustrates the use of the compositions of the present invention as excipients in making pharmaceutical tablets.

Tricalcium phosphate compacted and comminuted as in Example 10 was made into 0.75 gram pharmaceutical tablets with a hydraulic press with a dwell time of 60 seconds at various forces and tested for hardness on a Schleuniger tablet hardness tester with the results shown below:

| Tablet Molding Applied Load (Lbs.) | Hardness (SCU) |
|---|---|
| 2,500 (1134 kg.) | 9.5 |
| 5,000 (2268 kg.) | 18.5 |
| 7,500 (3401 kg.) | 27.5 |

As in the preceeding paragraph, dicalcium phosphate dihydrate compacted and comminuted as the tricalcium phosphate was in Example 8 in some cases using different forces and as in Example 9 were molded and tested with the following results:

| Tablet Molding Pressure (Atmospheres) | Hardness (SCU) Compaction kg/cm | | | | | |
|---|---|---|---|---|---|---|
| | Without Guar | | | With Guar | | |
| | 1610 | 2245 | 4465 | 1610 | 2245 | 4465 |
| 170 | 4.0 | 4.2 | 4.3 | 4.5 | 4.1 | 4.5 |
| 340 | 13.2 | 9.8 | 11.2 | 12.7 | 11.4 | 10.8 |
| 510 | 22.3 | 16.3 | 17.4 | 19.7 | 18.7 | 17.9 |

Having described the present invention and illustrated it in terms which are representative but not limiting, the scope of legal protection sought is given by the claims below.

I claim:

1. A mechanical process for treating calcium phosphate fine particles comprising compacting dry-mixed fine particles consisting essentially of calcium phosphate under pressure to form compacted calcium phosphate and comminuting the compacted calcium phosphate to granules suitable for use as an excipient for making pharmaceutical tablets.

2. The process described in claim 1 wherein the calcium phosphate is selected from the group consisting of dicalcium phosphate dihydrate, tricalcium phosphate, and calcium pyrophosphate.

3. The process described in claim 1 wherein the calcium phosphate is anhydrous monocalcium phosphate.

4. The process described in claim 1 wherein the calcium phosphate is monocalcium phosphate monohydrate.

5. The process described in claim 1 wherein the calcium phosphate is anhydrous dicalcium phosphate.

6. The process described in claim 1 wherein the calcium phosphate is tricalcium phosphate.

7. A mechanical process for treating fine particles consisting essentially of drymixed calcium phosphate which includes the step of compacting the particles under pressure to form a compacted calcium phosphate followed by the additional step of comminuting said compacted calcium phosphate to granules.

8. A mechanical process for treating fine particles consisting essentially of drymixed calcium phosphate which includes the step of compacting the particles under pressure to form a compacted calcium phosphate wherein the pressure ranges from about 4,000 to about 18,000 lbs. force per linear inch of roll width in a roller compactor.

9. A mechanical process for treating fine particles consisting essentially of drymixed calcium phosphate which includes the step of compacting the particles under pressure to form a compacted calcium phosphate wherein the pressure ranges from about 8,000 to about 14,000 lbs. force per linear inch of roll width in a roller compactor.

10. An improved mechanical process for forming granules from fine particles of calcium phosphate of less than 75 microns comprising compacting in a roller compactor particles consisting essentially of dry mixed calcium phosphate having a particle size of less than about 75 microns under pressure sufficient to form compacted calcium phosphate and comminuting said compacted calcium phosphate to form granules of a particle size larger than 75 microns.

* * * * *